US008785589B1

(12) United States Patent
Tan et al.

(10) Patent No.: US 8,785,589 B1
(45) Date of Patent: Jul. 22, 2014

(54) AZOBENZENE-CONTAINING GLASSY POLYIMIDES CAPABLE OF PHOTO-INDUCED LARGE-ANGLE BENDING AND METHODS OF MAKING THE SAME

(71) Applicant: The United States of America, as Represented by the Secretarty of the Air Force, Washington, DC (US)

(72) Inventors: Loon-Seng Tan, Centerville, OH (US); David Huabin Wang, Beavercreek, OH (US); Kyung Min Lee, Dayton, OH (US); Timothy J. White, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 13/866,551

(22) Filed: Apr. 19, 2013

Related U.S. Application Data (60) Provisional application No. 61/636,134, filed on Apr. 20, 2012, provisional application No. 61/636,170, filed on Apr. 20, 2012.

(51) Int. Cl.
*C08G 64/00* (2006.01)
*C08G 73/10* (2006.01)
*C08G 63/02* (2006.01)

(52) U.S. Cl.
CPC .................. *C08G 73/1085* (2013.01)
USPC ............................ 528/185; 564/305; 564/315

(58) Field of Classification Search
USPC .................... 564/305, 315; 528/185
See application file for complete search history.

(56) References Cited

U.S. PATENT DOCUMENTS

| | | |
|---|---|---|
| 3,455,879 A | 7/1969 | Gay et al. |
| 3,600,361 A | 8/1971 | Heacock et al. |
| 3,732,200 A | 5/1973 | Bach |
| 3,835,120 A | 9/1974 | Bach et al. |
| 4,107,125 A | 8/1978 | Lovejoy |
| 4,271,288 A | 6/1981 | Woo |
| RE30,922 E | 5/1982 | Heilman et al. |
| 4,394,499 A | 7/1983 | Robinson et al. |
| 4,728,697 A | 3/1988 | Bolon et al. |
| 4,981,497 A | 1/1991 | Hayes |
| 5,101,005 A | 3/1992 | Vora et al. |
| 5,175,234 A | 12/1992 | Lubowitz et al. |
| 5,300,559 A | 4/1994 | Sheehan et al. |
| 5,344,894 A | 9/1994 | Lubowitz et al. |
| 5,516,876 A | 5/1996 | Lubowitz et al. |
| 5,585,217 A | 12/1996 | Oba |
| 5,599,582 A | 2/1997 | Adamopoulous et al. |
| 5,670,651 A | 9/1997 | Tan et al. |
| 5,965,687 A | 10/1999 | Jensen |
| 6,001,277 A | 12/1999 | Ichimura et al. |
| 6,184,333 B1 | 2/2001 | Gray |
| 6,262,223 B1 | 7/2001 | Meador et al. |
| 6,307,008 B1 | 10/2001 | Lee et al. |
| 6,509,094 B1 | 1/2003 | Shah et al. |
| 7,582,722 B1 | 9/2009 | Tan et al. |

(Continued)

FOREIGN PATENT DOCUMENTS

| | | |
|---|---|---|
| EP | 2 380 867 A1 | 10/2011 |
| JP | 2005023151 | 1/2005 |
| JP | 2005154643 A | 6/2005 |
| JP | 2007051217 | 2/2007 |

OTHER PUBLICATIONS

Jenekhe, Samson A., et al., Nonlinear Optical Properties of Poly(p-phenylenebenzobisoxazole), Chem. Mater. 1992, 4, 683-687.

(Continued)

*Primary Examiner* — Terressa Boykin
(74) *Attorney, Agent, or Firm* — AFMCLO/JAZ; Rebecca Greendyke (57) ABSTRACT

Cross-linked polyimides based on a novel crosslinker and methods of making the same. The general structure of these heat-resistant and amorphous polyimides is shown as follows:

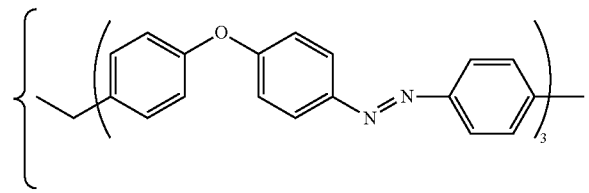
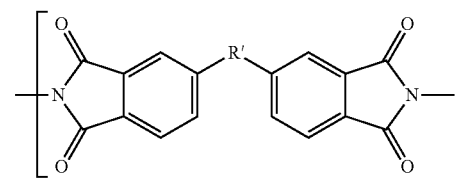
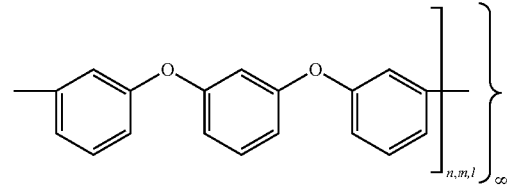

in which n, m, and l denote the degrees of polymerization (DP) of each arm and the linking group R' is one of the following moieties: —C(CF$_3$)$_2$—, —O—, —SO$_2$—, >C(=O), —OPh-C(CH$_3$)$_2$-PhO-, -(Ph)C(CF$_3$)—, or a direct bond (—). Films (cantilevers) comprising cross-linked polyimides according to the present invention demonstrate photodirected bending upon exposure to linearly polarized light.

14 Claims, 3 Drawing Sheets

(56) References Cited

U.S. PATENT DOCUMENTS

| | | | |
|---|---|---|---|
| 7,678,873 B1 | 3/2010 | Tan et al. | |
| 8,173,763 B1 | 5/2012 | Tan et al. | |
| 8,389,619 B1 | 3/2013 | Tan et al. | |
| 8,546,614 B1 * | 10/2013 | Tan et al. | 564/305 |
| 2003/0064235 A1 | 4/2003 | Okawa et al. | |
| 2004/0233377 A1 | 11/2004 | Utsumi et al. | |
| 2005/0080229 A1 | 4/2005 | Deets et al. | |
| 2006/0217482 A1 | 9/2006 | Lukehart et al. | |
| 2006/0235194 A1 | 10/2006 | Kato | |
| 2006/0270825 A1 | 11/2006 | Angermeier et al. | |
| 2007/0106056 A1 | 5/2007 | Itatani | |
| 2007/0270562 A1 | 11/2007 | Yamada et al. | |
| 2008/0025905 A1 | 1/2008 | Wang et al. | |
| 2008/0311303 A1 | 12/2008 | Naiki et al. | |
| 2009/0220722 A1 | 9/2009 | Wang | |
| 2010/0048745 A1 | 2/2010 | Yamada et al. | |
| 2011/0009513 A1 | 1/2011 | Chaudhary et al. | |
| 2011/0136061 A1 | 6/2011 | Itatani | |

OTHER PUBLICATIONS

Kannan, Ramamurthi, et al., Diphenylaminofluorene-Based Two-Photon Absorbing Chromophores with Various π-Electron Acceptors, Chem. Mater. 2001, 13, 1896-1904.
Pyun, Eumi, et al., "Kinetics and mechanisms of thermal imidization of a polyamic acid studied by ultraviolet-visible spectroscopy", Macromolecules (1989), 22(3), 1174-83.
Natansohn, A., et al., "Photoinduced Motions in Azo-Containing Polymers," Chemical Reviews (Washington, DC, United States) (2002), 102(11), 4139-4175.
Hugel, Thorsten, et al., "Single-molecule optomechanical cycle", Science (2002), 296(5570), 1103-1106.
Hosono, Nobuhiko, et al., "Photochemical control of network structure in gels and photo-induced changes in their viscoelastic properties" Colloids and Surfaces, B: Biointerfaces (2007), 56(1-2), 285-289.
Zhang, Chaohui, et al., "Rapid bending of a nonliquid crystal azobenzene polymer film and characteristics of surface relief grating" Journal of Applied Polymer Science (2009), 113(2), 1330-1334.
Kannan, Ramamurthi, et al., "Toward Highly Active Two-Photon Absorbing Liquids: Synthesis and Characterization of 1,3,5-Triazine-Based Octupolar Molecules," Chem. Mater. 2004, 16, 185-194.
He, Guang S., et al., "Degenerate Two-Photon-Absorption Spectral Studies of Highly Two-Photon Active Organic Chromophores," J. Chem. Phys., vol. 120 No. 11 (2004) 5275-5284.
Wang, David H., et al., "Photomechanical Response of Glassy Azobenzene Polyimide Networks" Macromolecules 2011, 44, pp. 3840-3846.
Hrozhyk, Uladzimir, et al., "Bidirectional Photoresponse of Surface Pretreated Azobenzene Liquid Crystal Polymer Networks," Optics Express, vol. 17, Issue 2, pp. 716-722 (2009).
Usami, Kiyoaki, et al., "Photo-Aligned Blend Films of Azobenzene-Containing Polyimides with and without Side-Chains for Inducing Inclined Alignment of Liquid Crystal Molecules," Journal of Applied Physics (2011), 110(4), 043522/1-043522/6.
Makita, Shonei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).
Lendlein Andreas et al., "Shape-Memory Polymers," Angewandte Chemie, International Edition, vol. 41, 2034-2057 (2002).
Liu C. et al., "Review of Progress in Shape-Memory Polymers," Journal of Materials Chemistry, vol. 17, 1543-1558 (2007).
Fay, Catherine C. et al., "Molecularly Oriented Polymeric Thin Films for Space Applications," High Performance Polymers, vol. 11, 145-156 (1999).
SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.

St. Clair, Anne K., et al. "Synthesis and Characterization of Essentially Colorless Polyimide Films," J. Polym. Mater. Sci Eng., vol. 51, pp. 62-66 (1984).
Miner, Gilda A., et al., "The Wettability of LaRC Colorless Polyimide Resins on Casting Surfaces," J. Polym. Mater. Sci Eng., vol. 76, pp. 381-382 (1997).
Straub, Daniel, "Lewis Structures of Boron Compounds Involving Multiple Bonding," J. Chem. Ed. 72(6) 494-497 (1995).
Chao, Tsung-Yi, et al., "Nonlinear Optical Polyimide/Montmorillonite/Nanocomposites Consisting of Azobenzene Dyes," Dyes and Pigments, 77 (2008) 515-524.
Agolini, F., et al., "Synthesis and Properties of Azoaromatic Polymers," Macromolecules (May-Jun. 1970), vol. 3, No. 3, 349-351.
Lovrien, R., "The Photoviscosity Effect," Proc. Natl. Acad. Sci. U.S. A. 1967 (57) 236-242.
Cojocariu, C., et al., "Light-induced motions in azobenzene-containing polymers," Pure Appl. Chem. 2004, 76, 1479-1497.
Tabiryan, N., et al., "Polymer film with optically controlled form and actuation," T. Optics Express 2005, 13, 7442-7448.
White, T.J., et al., "A high frequency photodriven polymer oscillator," J. Soft Matter 2008,4, 1796-1798.
Barrett, C.J., et al., "Photo-mechanical effects in azobenzene-containing soft materials," Soft Matter 2007, 3, 1249-1261.
Park, C., et al., "Actuating Single Wall Carbon Nanotube—Polymer Composites: Intrinsic Unimorphs," Adv. Mater. 2008, 20, 2074-2079.
Van Oosten, C.L., et al., "Bending Dynamics and Directionality Reversal in Liquid Crystal Network Photoactuators," Macromolecules 2008,41,8592-8596.
Irie, M., "Photochromism and Molecular Mechanical Devices," Bull. Chem. Soc. Jpn. 2008, 81 (8), 917-926.
Serak, S.V., et al., "Azobenzene liquid crystal polymer-based membrane and cantilever optical systems," Optics Express, vol. 17, No. 18 (Aug. 31, 2009), 15736-15746.
Hogan, P.M., et al., "UV-Manipulation of Order and Macroscopic Shape in Nematic Elastomers," Phys. Rev. E: Stat., Nonlinear, Soft Matter Phys. 2002, 65, 041720/1-041720110.
Eisenbach, C.D., "Isomerization of aromatic azo chromophores in poly(ethyl acrylate) networks and photomechanical effect," Polymer 1980, 21, 1175-1179.
Viswanathan, N.K., et al., "Surface relief structures on azo polymer films," J. Mater. Chem. 1999, 9, 1941-1955.
Harris, K.D., et al., Large amplitude light-induced motion in high elastic modulus polymer actuators, J. Mater. Chem. 2005, 15, 5043-5048.
Van Oosten, C.L., et al., "Glassy photomechanical liquid-crystal network actuators for microscale devices," Eur. Phys. J. E, 2007, 23, 329-336.
White, T.J., et al., "Polarization-controlled, photodriven bending in monodomain liquid crystal elastomer cantilevers," J. Mater. Chem. 2009, 19, 1080-1085.
Lee, K.M., et al., "Relationship between the Photomechanical Response and the Thermomechanical Properties of Azobenzene Liquid Crystalline Polymer Networks," Macromolecules 2010, 43, 8185-8190.
Finkelmann, H., et al., "A New Opto-Mechanical Effect in Solids," Phys. Rev. Lett. 2001, 87, 01550111-01550114.
Sroog, C.E., "Polyimides," Prog. Polym. Sci. 1991, 16, 561-694.
Koshiba, Y., et al., "Photo-induced alignment behavior of azobenzene compound in thin film," Thin Solid Films 2009, 518, 805-809.
Koerner, H., et al., "Photogenerating work from polymers," Mater. Today (Oxford, U. K.) 2008, 11, (7-8), 34-42.
Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.
Yu, Y., et al., "Photomechanical Effects of Ferroelectric Liquid-Crystalline Elastomers Containing Azobenzene Chromophores," Angew. Chem., Int. Ed. 2007, 46, 881-883.
Arlen, M., et al., "Thermal-Electrical Character of in Situ Synthesized Polyimide-Grafted Carbon Nanofiber Composites," Macromolecules 2008, 41, 8053-8062.

(56) References Cited

OTHER PUBLICATIONS

Chen, J.P., et al., "Highly Stable Optically Induced Birefringence and Holographic Surface Gratings on a New Azocarbazole-Based Polyimide," Macromolecules 1999, 32, 8572-8579.

Kumar, G.S., et al., "Photochemistry of Azobenzene-Containing Polymers," Chem. Rev. 1989, 89, 1915-25.

Yu, Y., et al., "Effect of Cross-linking Density on Photoinduced Bending Behavior of Oriented Liquid-Crystalline Network Films Containing Azobenzene," Chem. Mater. 2004, 16, 1637-1643.

Kondo, M., et al., "Effect of concentration of photoactive chromophores on photomechanical properties of crosslinked azobenzene liquid-crystalline polymers," J. Mater. Chem. 2010, 20, 117-122.

Li, M.-H., et al., "Light-Driven Side-On Nematic Elastomer Actuators," Adv. Mater. 2003, 15, 569-572.

U.S. Patent and Trademark Office, Non-Final Office Action mailed Sep. 26, 2012, U.S. Appl. No. 13/557,326, 9 pages.

U.S. Patent and Trademark Office, Non-Final Office Action mailed Mar. 27, 2013, U.S. Appl. No. 13/557,326, 5 pages.

U.S. Patent and Trademark Office, Non-Final Office Action mailed Nov. 7, 2013, U.S. Appl. No. 13/546,439, 9 pages.

Meador, Mary Ann B., et al., "Synthesis and Properties of Nanoporous Polyimide Aerogels Having a Covalently Bonded Network Structure," Polymer Preprints 2010, 51(1), 265.

Japanese Patent Office, Machine Translation of JP 2005154643A, 39 pages.

Meador, Mary Ann B., et al., "Improvements to the Synthesis of Polyimide Aerogels," ACS Spring National Meeting 2011, Anaheim, CA; Mar. 20-26, 2011, 34 pages.

Usami, K. et al., "Improvement in photo-alignment efficiency of azobenzene-containing polyimide films," Thin Solid Films 2009, 518, 729-734.

Usami, Kiyoaki, et al., "Pretilt Angle Control of Liquid Crystal Molecules by Photoaligned Films of Azobenzene-Containing Polyimide with Different Content of Side-Chain," Journal of Applied Phyics 104, 113528 (2008).

Lee, Kyung Min, and White, Timothy J., "Photomechanical Response of Composite Structures Built from Azobenzene Liquid Crystal Polymer Networks," Polymers (2011), 3, 1447-1457.

Georgiev, A., et al, "Polyimide Coatings Containing Azo-Chromophores as Structural Units," Journal of Physics, Conference Series vol. 113 No. 1 (2008) 012032.

Sakamoto, Kenji, et al., "Highly Polarized Polymer-Based Light Emitting Diodes Fabricated by Using Very Thin Photoaligned Polyimide Layers," Journal of Applied Physics 107, 113108 (2010).

Sakamoto, Kenji, et al., "Light Exposure Dependence of Molecular Orientation of Glassy Polyfluorene Layers Formed on Photo-Aligned Polyimide Films," Colloids and Surfaces B: Biointerfaces 56, pp. 260-264 (2007).

Usami, K., et al., "Stability of Photo-Induced Alignment of Azobenzene-Containing Polyimides," Molecular Crystals and Liquid Crystals (2005) 438:1, 227/[1791]-236[1800].

Park, B., et al., "Thermal and Optical Stabilities of Photoisomerizable Polyimide Layers for Nematic Liquid Crystal Alignments," Jpn. J. Appl. Phys. vol. 37 (1998) pp. 5663-5668.

Cain, J. C., "Para- and Meta-nitrosoacetanilide," J. Chem. Soc., Trans. 1908, 93, 681-684.

Yu, Y., et al., "Precisely Direction-Controllable Bending of Cross-Linked Liquid-Crystalline Polymer Films by Light," Mol. Cryst. Liq. Cryst., vol. 436, pp. 281/[1235]-290/[1244], 2005.

Si, J., et al., "Thermosetting enhancement of the light-induced polar orientation stability of molecules in polymers," J. Appl. Phys. 85, 8018 (1999); doi: 10.1063/1.370637.

Eisenbach, C. D., "Relation between Photochromism of Chromophores and Free vol. Theory in Bulk Polyers," Ber. Bunsenges. Phys. Chem. 1980, 84, 680.

Pieroni, O., et al., "Photoresponsive Polymeric Materials," Trends Polym. Sci. (Cambridge, U.K.) 1995, 3, 282-287.

Mathisen, R., et al., "Imidization studies of polyamic acids by dye-labeling technique," Polymer Preprints (American Chemical Society, Division of Polymer Chemistry) (1987), 28(1), 82-83.

Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.

Yager, K. G., et al., "Azobenzene Polymers as Photomechanical and Multifunctional Smart Materials," Intelligent Materials, Shahinpoor, M. and Schneider, H.-J., Eds., Royal Society of Chemistry: Cambridge, UK, 2008; pp. 424-446.

Irie, M, et al., "Photoresponsive Polymers," Functional Monomers and Polymers, 2nd ed., Takemoto, K., et al., Eds., Dekker: New York, 1997, pp. 65-116.

Tan, Loon-Seng, et al., U.S. Appl. No. 13/557,326, filed Jul. 25, 2012.

Tan, Loon-Seng, et al., U.S. Appl. No. 13/546,439, filed Jul. 11, 2012.

Tan, Loon-Seng, et al., U.S. Appl. No. 13/661,194, filed Oct. 26, 2012.

\* cited by examiner

AZOBENZENE-CONTAINING GLASSY POLYIMIDES CAPABLE OF PHOTO-INDUCED LARGE-ANGLE BENDING AND METHODS OF MAKING THE SAME

CROSS-REFERENCE TO RELATED APPLICATIONS

This application claims the benefit of U.S. Provisional Patent Application No. 61/636,134, filed on Apr. 20, 2012, by inventor Loon-Seng Tan, et al., entitled "Multi(Azobenzene-Amine) Photo-Active Crosslinkers," and U.S. Provisional Patent Application No. 61/636,170, filed Apr. 20, 2012, by inventor Loon-Seng Tan, et al., entitled "Azobenzene-Containing Glassy Polyimides Capable of Photo-Induced Large-Angle Bending," both of which are incorporated herein by reference in their entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention relates to cross-linked, imide-based, photomechanical polymers derived from a multi(azobenzene-amine) cross-linker in conjunction with an aromatic amine and an aromatic dianhydride.

2. Description of the Related Art

Photomechanical polymers are a special class of smart (stimuli-responsive) polymers that are responsive to light and are capable of generating photo-directed motions and dimensional or shape alteration at the macro-scale level. These motions and/or alterations are driven by the collective molecular-volume change brought about by the chromophoric units upon appropriate irradiation. The chromophoric units in photoresponsive polymers are photochromic and have the unique ability to reversibly interconvert between two structural isomers (each with distinctly different optical and physical properties) under appropriate excitation conditions. Examples of chromophoric units can be found in photo-isomerizable molecules such as azobenzenes, spiropyrans, spirooxazines, diarylethylenes, and fulgides. However, with respect to photomechanical polymers, azobenzene is the most commonly used molecularly-actuating moiety because of its excellent thermal stability and resolved isomeric forms, as well as its ability to form surface gradient reliefs when subjected to conventional or polarization holography.

The resulting photomechanical output of a polymeric material depends not only on its optical properties (absorption wavelength, wavelength of exposure, polarization of exposure), but also on its molecular architecture and morphology (amorphous, crystalline, liquid crystalline). In addition, the photomechanical output is dependent on the polymeric material's thermomechanical properties, as well as the geometrical properties of the device, e.g. thickness of a cantilever.

Polyimides (PIs) represent an important class of heat-resistant polymers that have found utility in a wide spectrum of applications, ranging from structural components to electronic and photonic devices. The widespread application of polyimides is mainly the result of their excellent combination of physical properties, thermal stability, and processability. For example, polyimides containing azobenzene in the backbone or side-chain have been investigated for photo-induced alignment in liquid crystal display (LCD) as well as nonlinear optical applications. More recently, an azobenzene-containing poly(amic acid) (a PI precursor) was crosslinked by a triamine in N,N-dimethylformamide (DMF) and the resulting sol-gels showed a two-fold increase in the storage modulus after irradiation with 405 nm light. Another closely related aromatic poly(amic acid) was reported to be photomechanically active.

SUMMARY OF THE INVENTION

In accordance with the present invention, there is provided a composition of matter comprising non-liquid-crystalline, amorphous polyimides containing a photo-active tris(azobenzene) crosslinker. Cantilevers comprising these polyimides demonstrate large-amplitude, photo-directed, bidirectional bending. The general formula for the subject crosslinked polyimides is provided below:

In the general formula, "n,m,l" denote the degrees of polymerization (DP) of each of the three branches of the crosslinked polyimide. In one embodiment, n, m, and l are equal. In another embodiment, one or more of n, m, and l is not equal with respect to one another. In a further embodiment, the DP range is about 2 to about 20. In another embodiment, the DP range is about 3 to about 15. The linking group R' is one or more of the following moieties: —C(CF$_3$)$_2$—, —O—, —SO$_2$—, >C(=O), —OPh-C(CH$_3$)$_2$-PhO-, or -(Ph)C(CF$_3$)—. In other embodiments, one or more of the linking groups R' may simply be a direct bond (—) between the two phthalimido moieties.

The present invention further includes a method for making the crosslinked polyimides comprising the following steps: dissolving 1,3-bis(3-aminophenoxy)benzene and a bis (phthalic anhydride) compound in N,N-dimethylacetamide (DMAc) to form a solution, with the bis(phthalic anhydride) compound having the general formula of:

stirring the solution under a nitrogen atmosphere at room temperature to form a poly(amic acid) oligomer (PAA) solution in which the PAA oligomers further comprise terminal anhydride groups;—adding a tris(azobenzene-amine) crosslinker to the poly(amic acid) oligomer solution, wherein the tris(azobenzene-amine) cross-linker has a general structure:

wherein for the cross-linker, for meta-azo substitution, R is equal to H, and for para-azo substitution, R is selected from the group consisting of H, F, Cl, $CF_3$, and $CH_3$; allowing the tris(azobenzene-amine) cross-linker to dissolve in the poly(amic acid) oligomer solution to form a poly(amic acid) sol-gel precursor; and curing the poly(amic acid) sol-gel precursor to crosslink and imidize the poly(amic acid) sol-gel precursor to form the crosslinked polyimide.

In one embodiment of the method, the molar ratio of the bis(phthalic anhydride) compound to the 1,3-bis(3-aminophenoxy)benzene ranges, respectively, from about 1.00:0.92 to about 1.00:0.55. In various alternative embodiments of the method, the bis(phthalic anhydride) compound may be 2,2-bis(phthalic anhydride)-1,1,1,3,3,3-hexafluoroisopropane; 4,4'-oxydiphthalic anhydride; 3,3',4,4'-benzophenonetetracarboxylic dianhydride; 3,3',4,4'-diphenylsulfone tetracarboxylic dianhydride; 2,2-bis[4-(3,4-dicarboxyphenoxy)phenyl]propane dianhydride; 4,4'-(2,2,2-trifluoro-1-phenylethylidene)diphthalic anhydride; or 3,3',4,4'-biphenyl-tetracarboxylic dianhydride.

DETAILED DESCRIPTION

It has been estimated that the mechanical work per polymer chain based on the azobenzene isomerization process is only 10% efficient, meaning that only 10% of the incident photon energy ($4 \times 10^{-19}$ J) is converted to mechanical work ($-4.5 \times 10^{-20}$ J). As a way to improve the transduction efficiency via increasing the effective number density of azobenzene-actuating units in a polyimide (PI) network structure, the presently disclosed crosslinker is designed to contain three azobenzenes per molecule, via a trifunctional monomer, which can promote polyimide network formation under appropriate fabricating and curing conditions.

As an example, a representative synthesis of a photo-active, multi-(azobenzene-amine) cross-linker according to the present invention (compound 6) is shown in Scheme 1 below.

Scheme 1. Synthesis of a tris(azobenzene-amine) monomer (6) and tris(N-phthalimide)-endcapped model compound (7)

7

Scheme 1. Synthesis of a tris(azobenzene-amine) monomer (6) and tris(N-phthalimide)-endcapped model compound (7)

In Scheme 1,1,1,1,-tris(4-hydroxyphenyl)ethane (compound 1) was treated with 1-fluoro-4-nitrobenzene in presence of potassium carbonate to make 1,1,1-tris[4-(4-nitrophenoxy)phenyl]ethane (compound 2), which was reduced to 1,1,1-tris[4-(4-aminophenoxy)phenyl]ethane (compound 3) by catalytic hydrogenation. The reaction of compound 3 and 4-nitrosoacetanilide (compound 4) in acetic acid yielded the tris(azobenzene-amide) as compound 5. The tris(azobenzene-amine) monomer (compound 6) was generated after the deprotection of compound 5 via alkaline deacetylation reaction. By end-capping compound 6 with phthalic anhydride, a tris(azobenzene-N-phthalimide) model compound (compound 7) was obtained (see Scheme 1 above), which was useful in validating and semi-quantifying the kinetics of photoisomerization process in the cross-linked azo-polyimide system.

The crosslinked polyimides of the present invention may be made using the following general method. The method begins by dissolving 1,3-bis(3-aminophenoxy)benzene and a bis(phthalic anhydride) compound in N,N-dimethylacetamide (DMAc) to form a solution, with the bis(phthalic anhydride) compound having the general formula of:

Next, the solution is stirred under a nitrogen atmosphere at room temperature to form a poly(amic acid) oligomer (PAA) solution in which the PAA oligomers further comprise terminal anhydride groups. A tris(azobenzene-amine) cross-linker having the following general structure is then added to the poly(amic acid) oligomer solution:

In the cross-linker, for meta-azo substitution, R is equal to H, and for para-azo substitution, R is selected from the group consisting of H, F, Cl, $CF_3$, and $CH_3$. The azo linkage is para to phenoxy group. As described in more detail with respect to Scheme 2, an excess amount of the bis(phthalic anhydride) compound is required to prepare the desired poly(amic acid) oligomers (PAA) with terminal anhydride groups, and the added amount of crosslinker ranges from 5 to 30 mol % in accordance with ⅓ of the calculated total molar amount of the terminal anhydride groups of PAA to form a PAA sol-gel precursor. The method continues with allowing the tris (azobenzene-amine) cross-linker to dissolve in the poly(amic acid) oligomer solution to form a poly(amic acid) sol-gel precursor; and curing the poly(amic acid) sol-gel precursor to crosslink and imidize the poly(amic acid) sol-gel precursor to form a crosslinked polyimide with the following general structure:

The tris(azobenzene-amine) cross-linker crosslinker creates crosslinked polyimides containing three branches, with varying degrees of polymerization (DP) for each branch, which are denoted as "n,m,l." The DP represents the number of repeat units (contained in the brackets in the general structure above) that each branch contains. The DP values may be the same or different for each branch, with even spacing between the repeat units. Where the DP values are all equal, the resulting polymer network is uniform. In one embodiment, the DP may be between about 2 and about 20. In another embodiment, the DP may be between about 3 and about 15. The infinity symbol (∞) is used to denote an infinite network structure for a crosslinked polymer. The linking group R' may be one or more of the following moieties: —$C(CF_3)_2$—, —O—, —$SO_2$—, >C(=O), —OPh-$C(CH_3)_2$-PhO-, or -(Ph) $C(CF_3)$—. In other embodiments, one or more of the linking groups R' may simply be a direct bond (—) between the two phthalimido moieties.

The bis(phthalic anhydride) compound may be 2,2-bis(phthalic anhydride)-1,1,1,3,3,3-hexafluoroisopropane; 4,4'-oxydiphthalic anhydride; 3,3',4,4'-benzophenonetetracarboxylic dianhydride; 3,3',4,4'-diphenylsulfone tetracarboxylic dianhydride; 2,2-bis[4-(3,4-dicarboxyphenoxy)phenyl]propane dianhydride; 4,4'-(2,2,2-trifluoro-1-phenylethylidene)diphthalic anhydride; or 3,3',4,4'-biphenyl-tetracarboxylic dianhydride. In one embodiment of the method, the molar ratio of the bis(phthalic anhydride) compound to the 1,3-bis(3-aminophenoxy)benzene ranges from about 1.00:0.92 to about 1.00:0.55.

More specifically, the crosslinked polyimides of the present invention are related to a well-known low-color, space-grade polyimide commonly known as CP2 (LaRC™-CP2, originally developed by NASA Langley Research Center). CP2 may be derived from 2,2-bis(phthalic anhydride)-1,1,1,3,3,3-hexafluoroisopropane (6FDA) and 1,3-bis(3-aminophenoxy)benzene (APB). Scheme 2 outlines the synthesis of an exemplary azobenzene containing CP2 (azo-CP2) polyimide. 6FDA (compound 8) and APB (compound 9) were dissolved under nitrogen atmosphere in N,N-dimethylacetamide (DMAc) (5 wt % concentration) at room temperature for 24 hours with excess 6FDA for the preparation of poly(amic acid) oligomers (PAA oligomers, compound 10) with terminal anhydride groups. Subsequently, the tris (azobenzene-amine) crosslinker (compound 6) was added to the solution of anhydride-terminated PAA oligomers with a stoichiometric ratio of the amino group to the terminal acid anhydride. After the crosslinker had completely dissolved, the resulting PAA sol-gel precursor/DMAc (compound 11, structure not shown) was poured onto glass slides and cured in an oven up to 300° C. to crosslink and imidize the polymer films to form a azobenzene-containing CP2 polyimide network (compound 12).

crosslinker that was added must contain a balancing amount of amine groups to react with all the anhydride end-groups (i.e. two per PAA chain). For example, to generate the Azo-CP2-03 sample that contains 3 mol % of crosslinker (see Table 1), the dianhydride-terminated PAA oligomers were Scheme 2. Synthesis of an exemplary azobenzene-containing CP2 polyimide network.

Crosslinked CP2 films containing three-arm azobenzene net points n, m, l: DP of each arm Crosslinked CP2 Films Containing Three-Arm Azobenzene Net Points n,m,l: DP of Each Arm Scheme 2. Synthesis of an Exemplary Azobenzene-Containing CP2 Polyimide Network According to the principle of polymerization, the amount of crosslinker added must generally be such that the functionality molar ratio of all of the amine groups (three from the crosslinker and two from the diamine APB) to all of the anhydride groups (two from 6FDA) is 1:1; i.e. amine:anhydride is 1:1. Because the initial PAA oligomers were synthesized using excess dianhydride (e.g. 6FDA), the amount of first prepared from 100 mol % of the dianhydride, 6FDA, and 95.5 mol % of the diamine, APB. Because there are two anhydride endgroups, there are a total of 2×(100-95.5) 9 mol % of anhydride. Because each molecule of crosslinker (three amines) can react with three anhydride endgroups, the molar amount of crosslinker required is ⅓ of 9 mol % of the total anhydride endgroups.

The concentration of azobenzene may be varied in the azo-CP2 films by adding various amounts (i.e. 5, 10, 20 and 30 mol %) of the tris(azobenzene-amine) monomer to the respective PAA/DMAc solutions. The molar ratios of the three monomer mixtures, 6FDA: APB: crosslinker, are listed in Table 1. The film thickness for the azo-CP2 sample, as an example of photo-mobile cantilever for this series of crosslinked azo-polyimides, is 20 μm.

The following examples and methods are presented as illustrative of the present invention or methods of making or carrying out the invention and are not restrictive or limiting of the scope of the invention in any manner. The crosslinked, azobenzene-containing polyimides according to the present invention may be synthesized following the procedures given in the following examples.

Example 1

Synthesis of 1,1,1-Tris[4-(4-nitrophenoxy)phenyl]ethane

Into a 250 mL three-necked flask equipped with a magnetic stir bar and nitrogen inlet and outlet were placed 1,1,1,-tris (4-hydroxyphenyl)ethane (10.0 g, 33.0 mmol), 1-fluoro-4-nitrobenzene (15.4 g, 109 mmol), potassium carbonate (15.1 g, 109 mmol) and DMF (100 mL). The mixture was stirred at room temperature for 24 hours and filtered. The filtrate was diluted with ethyl acetate (400 mL) and the organic layer was separated. The organic layer was washed with water 3 times. It was dried over anhydrous magnesium sulfate and filtered. The filtrate was concentrated to 75 mL on a rotary evaporator, and then stored in refrigerator for several days to afford 11.2 g (51%) of off-white crystals, m.p. 98-99° C. MS (m/e): 669 ($M^+$). Anal. Calcd. for $C_{38}H_{27}N_3O_9$: C, 68.18%; H, 4.06%; N, 6.27%; O, 21.50%. Found: C, 67.69%; H, 4.26%; N, 6.21%; O, 21.22%. FT-IR (KBr, $cm^{-1}$): 3076, 2979, 1586, 1513, 1486, 1344, 1248, 1165, 1107, 874, 846. $^1$H-NMR (DMSO-$d_6$, δ in ppm): 2.26 (s, 3H, $CH_3$), 7.17-7.27 (m, 18H, Ar—H), 8.28-8.31 (d, 6H, Ar—H).

Example 2

Synthesis of 1,1,1-Tris[4-(4-aminophenoxy)phenyl]ethane 1,1,1-Tris[4-(4-nitrophenoxy)phenyl]ethane (Example 1; 3; 5.0 g, 7.5 mmol), THF (50 mL) and 5% palladium on activated carbon (0.50 g) were added to a hydrogenation bottle. The bottle was secured on a Parr hydrogenation apparatus, flushed three times with hydrogen, and then pressurized to 55 psi. After the mixture had been agitated at room temperature for 24 hours under the hydrogen pressure of 55 psi, it was filtered through Celite. The filter cake was washed with THF, and then the filtrate was evaporated to dryness on a rotary evaporator to afford a 4.25 g (98%) of yellow crystal, which was used without further purification, m.p. 220-221° C. MS (m/e): 579 ($M^+$). Anal. Calcd. for $C_{38}H_{33}N_3O_3$: C, 78.73%; H, 5.74%; N, 7.25%. Found: C, 78.17%; H, 5.78%; N, 7.04%. FT-IR (KBr, $cm^{-1}$): 3441, 3361 ($NH_2$), 3035, 2970, 1617, 1581, 1497, 1384, 1232, 1173, 1117, 1010, 871, 842. $^1$H-NMR (DMSO-$d_6$, δ in ppm): 2.02 (s, 3H, $CH_3$), 4.99 (s, 6H, $NH_2$), 6.53-6.58 (d, 6H, Ar—H), 6.68-6.74 (m, 12H, Ar—H), 6.88-6.93 (d, 6H, Ar—H).

Example 3

Synthesis of N-(4-nitrosophenyl)acetamide

After oxone (potassium peroxymonosulfate, from Sigma-Aldrich®; 12.28 g, 20.0 mmol) had dissolved completely in water (100 mL), potassium carbonate (4.14 g, 30 mmol) was added slowly to neutralize the solution to a weak acidity. The solution was added quickly into a solution of 4'-aminoacetanilide (from Sigma-Aldrich®; 1.50 g, 10.0 mmol) in water (150 mL). The mixture immediately turned green, and greenish-gray solids started to fall out of solution. After the mixture had been stirred for another 10 minutes, the precipitates were collected on a filter funnel, air dried, and recrystallized from hot ethanol. Two batches of products were collected to give a total yield of 1.06 g (65%) greenish crystals, mp 179-180° C. (lit. 179-180° C.).

Example 4

Synthesis of 1,1,1-tris{4-[4-(4-acetamidophenyldiazenyl)phenoxy]phenyl}ethane 1,1,1-Tris(4-(4-aminophenoxy)phenyl)ethane (Example 2; 0.580 g, 1.00 mmol), N-(4-nitrosophenyl)acetamide (Example 3; 0.985 g, 6 mmol) and acetic acid (20 mL) were charged into a 150 mL round-bottomed flask equipped with a magnetic stir bar. The mixture was stirred at room temperature for 48 hours. The mixture was at first turned into a greenish solution, and then yellow particles started to precipitate out of the solution. The mixture was diluted by deionized water (100 mL). Solids were collected and washed with water (500 mL), followed by ethanol (200 mL) to remove most of the unreacted nitroso reagent. The solid was then extracted by hot acetone (100 mL) four times. The acetone extract was concentrated on a rotary evaporator to give yellow solids as raw product. The raw product was slurried in hot ethanol (50 mL) and filtered twice after cooling to room temperature in between to give 0.62 g (61%) of yellow solids, mp 220° C. (dec.). $^1$H-NMR ($d_6$-DMSO, δ in ppm): 2.09 (s, 9H, $COCH_3$), 2.15 (s, 3H, $CCH_3$) 7.03-7.15 (m, 18H), 7.79-7.87 (m, 18H) 10.28 (s, 3H, NHCO). $^{13}$C-NMR ($d_6$-DMSO, δ in ppm): 24.16, 30.28, 51.00, 118.50, 118.86, 119.18, 123.42, 124.35, 129.99, 142.09, 144.50, 147.38, 147.77, 153.78, 159.07, 168.06.

Example 5

Synthesis of 1,1,1-tris{4-[4-(4-aminophenyldiazenyl)phenoxy]phenyl}ethane

To a 100 mL round-bottomed flask with a stir-bar and a condenser, 1,1,1-tris[4-(4-(4-acetamidophenyldiazenyl)phenoxy)phenyl]ethane (Example 4; 0.50 g, 0.49 mmol), 6 M HCl (20 mL) and 95% ethanol (20 mL) were charged and heated to 80° C. The mixture was stirred at 80° C. for 3 days. After the mixture was allowed to cool to room temperature, water (60 mL) added. The resulting red solid was collected by filtration and washed with dilute sodium bicarbonate solution, followed by deionized water (300 mL). After being air dried, the crude product was purified by column chromatography (silica gel, ethyl acetate as eluent). The solvent was removed by a rotary evaporator to afford 0.23 g (52.5%) of orange red solid, mp >300° C. MS (m/e): 892 ($M^+$). Anal. Calcd. for $C_{56}H_{45}N_9O_3$: C, 75.40%; H, 5.08%; N, 14.13%. Found: C, 75.44%; H, 5.08%; N, 13.98%. $^1$H-NMR ($d_6$-DMSO, δ in ppm): 2.12 (s, 3H, $CCH_3$), 6.03 (s, 6H, $NH_2$), 6.67-6.70 (d, 6H, J=8.7 Hz), 6.99-7.02 (d, 6H, J=8.7 Hz), 7.09-7.13 (m, 12H), 7.62-7.66 (d, 6H, J=8.7 Hz), 7.75-7.78 (d, 6H, J=8.7 Hz). $^{13}$C-NMR ($d_6$-DMSO, δ in ppm): 30.34, 51.91, 113.41, 118.44, 118.69, 123.52, 124.96, 129.93, 142.92, 144.25, 148.41, 152.56, 154.21, 157.75.

Example 6

Representative Procedure for the Synthesis of Azobenzene-Containing Polyimides (20 Mol %)

1,3-Bis(3-aminophenoxy)benzene (APB; 0.4093 g, 1.400 mmol) and DMAc (8 mL) were added to a 50 mL 3-necked flask equipped with a magnetic stirrer and a nitrogen inlet and outlet and stirred under dry nitrogen at room temperature for 30 minutes. 2,2-Bis(phthalic anhydride)-1,1,1,3,3,3-hexafluoroisopropane (6FDA; 0.8885, 2.000 mmol) was then introduced to the resulting solution. The light yellow solution was agitated at room temperature for 24 hours to afford a poly (amic acid) solution. Then, the tris(azobenzene-amine) crosslinker (Example 5; 0.3568 g, 0.400 mmol) was added to this solution. After the crosslinker had completely dissolved in DMAc, the mixture was poured into a glass petri dish, followed by vacuum evaporation of DMAc at 50° C., and heat-treated according to following schedule: 100° C./2 hrs, 150° C./2 hrs, 175° C./1 hr, 200° C./2 hrs, 250° C./1 hr and 300° C./1 hr to form polyimide films. The film thickness was approximately 20 µm. To prepare a polyimide with (ax100) mol % of the crosslinker, this procedure was followed with variation in the mole ratio of APB: 6FDA:crosslinker=(1-3a/2):1:a, where a can be varied from 0.05 to 0.50. In the designation, azo-CP2-XX, the "XX" corresponds to the mol % of the azobenzene-containing crosslinker, ranging from 5-30 mol %

Table 1 below summarizes the composition and properties of polyimide films made according to the present invention.

TABLE 1

Composition and Physical Properties of Azobenzene-Containing Polyimides and Copolyimides

| Sample | 6FDA (mol %) | APB (mol %) | Cross-linker (mol %) | $T_g$ (° C.) | E (GPa) | $M_c$ (Dalton) | $\alpha_{442}$ (cm$^{-1}$) |
|---|---|---|---|---|---|---|---|
| CP2 | 100 | 100 | 0 | 219 | 1.9 ± 0.1 | — | — |
| Azo-CP2-03 | 100 | 95.5 | 3 | — | — | 15,827 | — |
| Azo-CP2-05 | 100 | 92.5 | 5 | 220 | 1.6 ± 0.2 | 9,592 | 379 |
| Azo-CP2-10 | 100 | 85 | 10 | 226 | 1.8 ± 0.2 | 4,916 | 470 |
| Azo-CP2-20 | 100 | 70 | 20 | 246 | 2.4 ± 0.3 | 2,578 | 563 |
| Azo-CP2-30 | 100 | 55 | 30 | 284 | 2.9 ± 0.3 | 1,799 | 650 |
| Azo-CP2-40 | 100 | 40 | 40 | — | — | 1,409 | — |

In Table 1, the measured thickness of the azo-CP2 films are as follows: 18 µm (azo-CP2-05), 21 µm (azo-CP2-10), 21 µm (azo-CP2-20) and 20 µm (azo-CP2-30). The cantilevers were uniform in thickness with variation less than 0.5 µm. $T_g$ is measured from the peak of tan delta (DMA) as an average value taken from four measurements. The modulus (E) is determined in tension at 25° C. as an average from five specimens per sample. $M_c$ denotes the average molecular weight of the linear segment between two cross-linked sites, calculated from the following equation $M_c=350.27 \times X_n+295.32 \times 2$, where 350.27 is one-half the formula weight of a CP2 repeat unit, the number-average degree of polymerization $X_n=(1+r)/(1-r)$, the stoichiometric imbalance factor (r) is the molar ratio of diamine to dianhydride, and 295.32 is one-third value of the formula weight of cross-linker segment (from methyl-end to imide-nitrogen) in CP2 network. $\alpha_{442}$ is the measured absorption coefficient for the materials at 442 nm. Azo-CP2-03 and Azo-CP2-40 were extrapolated cross-linked polyimide compositions to define the range of degrees of polymerization (DP, which is indicated by n,m,l in the generic structure for Azo-CP2-XX) for linear CP2 segments. Because the molecular weight for a CP2 repeat unit is ~700 Da, the calculated DP values are (from top to bottom): 23, 14, 7, 4, and 3.

While the crosslinking density increases as the crosslinker concentration increases, the calculated average molecular weights between crosslinked sites ($M_c$), on the other hand, follows an opposite trend (see Table 1 above). The glass transition temperature ($T_g$) of neat polyimide (CP2) is 214° C. by DMA. Comparatively, the $T_g$ values (220-284° C.) of the azobenzene-containing polyimide networks (i.e. azo-CP2-XX, increase with the concentration of tris(azobenzene) crosslinker, especially with concentrations >5 mol %. The tensile moduli (E) of the azo-CP2 films initially decrease with the presence of crosslinker concentration (0-5 mol %) as compared to that of unmodified CP2, before subsequently increasing by ~0.2-0.3 GPa per 5 mol % of crosslinker added. It is speculated that at the crosslinker concentration of <5 mol % the tripod geometry of the crosslinker may be disrupting the chain-packing regularity of the CP2 polyimide, resulting in softening of the azo-CP2 networks. However, in the azo-CP2 systems, increasing crosslink density (and the corresponding decrease in $M_c$ between the azobenzene net points) causes the increase in modulus with each addition of 5 mol % crosslinker.

Example 7

Photomechanical Characterization of Cantilevers Comprising Azo-CP2-20

Figure 1A:
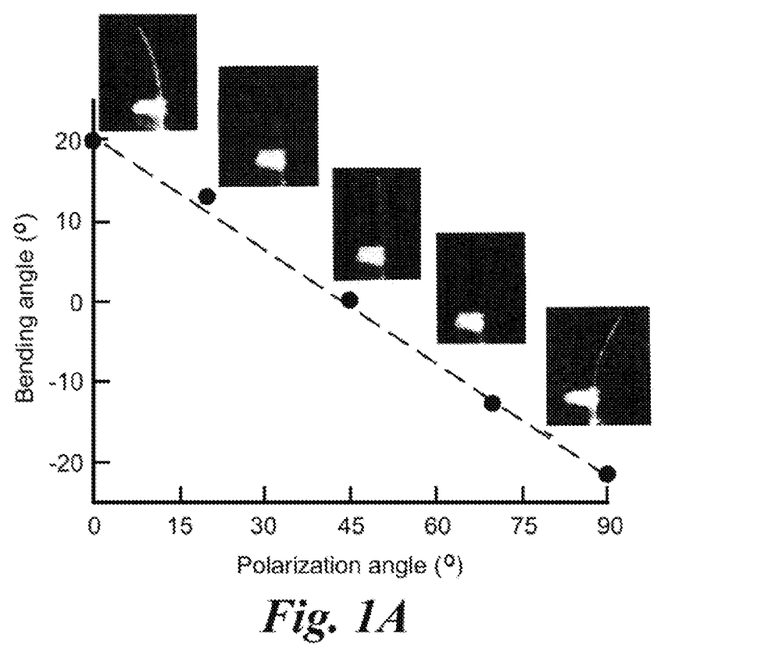
FIG. 1A illustrates the bending angle as a function of the polarization angle (angle between polarization direction of linearly polarized light and long axis of cantilever) and time for a cantilever composed of an azobenzene-containing polyimide network variant according to the present invention (azo-CP2-20) in response to exposure to a 120 $mW/cm^2$ 442 nm light source.
Figure 1B:
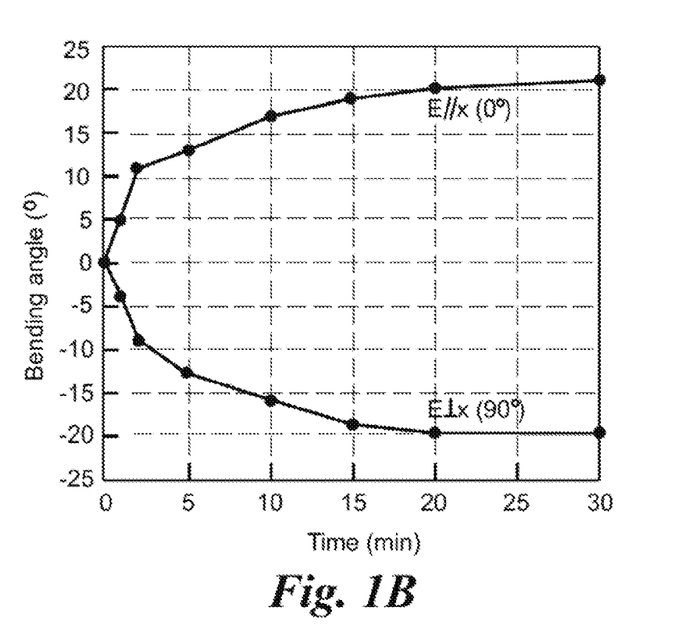
FIG. 1B illustrates the bending angle as a function of the time for a cantilever comprising azo-CP2-20 in response to exposure to a 120 $mW/cm^2$ 442 nm light source.

The photomechanical response of the azo-CP2-20 cantilevers is depicted in FIGS. 1A and 1B, which plot the magnitude of bending angle against polarization angle on exposure to a linearly polarized blue laser of 442 nm in wavelength with an intensity of 120 mW/cm$^2$. The direction of the laser exposure in the images presented here is from left to right. Interestingly, despite the extremely glassy nature of the azo-CP2-20 network, the cantilever bends more than 20° when exposed to the light polarized parallel to the long axis (E//x, 0°) of the cantilever. As the polarization angle is shifted from 0° to 15°, the magnitude of bending decreases. When the polarization of the laser is 45° to the long axis of the cantilever, no bending is observed. At polarization angles greater than 45°, bending occurs in the reverse direction with greatest magnitude occurring when the azo-CP2-20 cantilever is exposed to light polarized orthogonal to the long axis of the cantilever (E⊥x, 90°). Importantly, both the forward and reverse bending directions are uniform and symmetrical. As evident in FIGS. 1A and 1B, exposure to the 442 nm laser allows for polarization-controlled, reversible forward and backward motion, with remote and precise control of the bending angle.

Linearly polarized blue-green (440-510 nm) light induces what has been referred to as trans-cis-trans reorientation (also known as the Weigert effect). This phenomenon has been extensively employed in glassy azobenzene polymers to form both conventional volume gratings as well as surface relief gratings. Fundamental to this mechanism is the simultaneous and repeated trans-cis and cis-trans isomerization cycles of azobenzene induced by light in this wavelength regime. The repeated trans-cis and cis-trans isomerizations of azobenzene, due to the dichroic absorption of azobenzene (in addition to the rotational freedom of the azo bond when photoexcited) results in a statistical buildup of trans azobenzene rotated orthogonal to the incident linear polarization of the light source. Due to the large absorption coefficient of azo-CP2-20 at 442 nm (see Table 1), light is absorbed nonuniformly across the thickness of the film. When light is polarized parallel to the long axis of the cantilever, the reorientation of azobenzene results in a contraction along this long axis, which yields bending towards the light source. Conversely, when light is polarized orthogonal to the long axis of the cantilever, the reorientation of azobenzene causes an expansion along the long axis, which yields bending away from the laser source. The fact that bending is not observed to light polarized 45° to the long axis confirms that a) the mechanism is not photothermal in nature, and b) it is the expected result of a reorientation mechanism (no net change in reorientation). Calculations indicate that only a small percentage of the azobenzene mesogens need to rotate to generate the strain required to drive bending of this magnitude in this glassy system.

Figure 2:
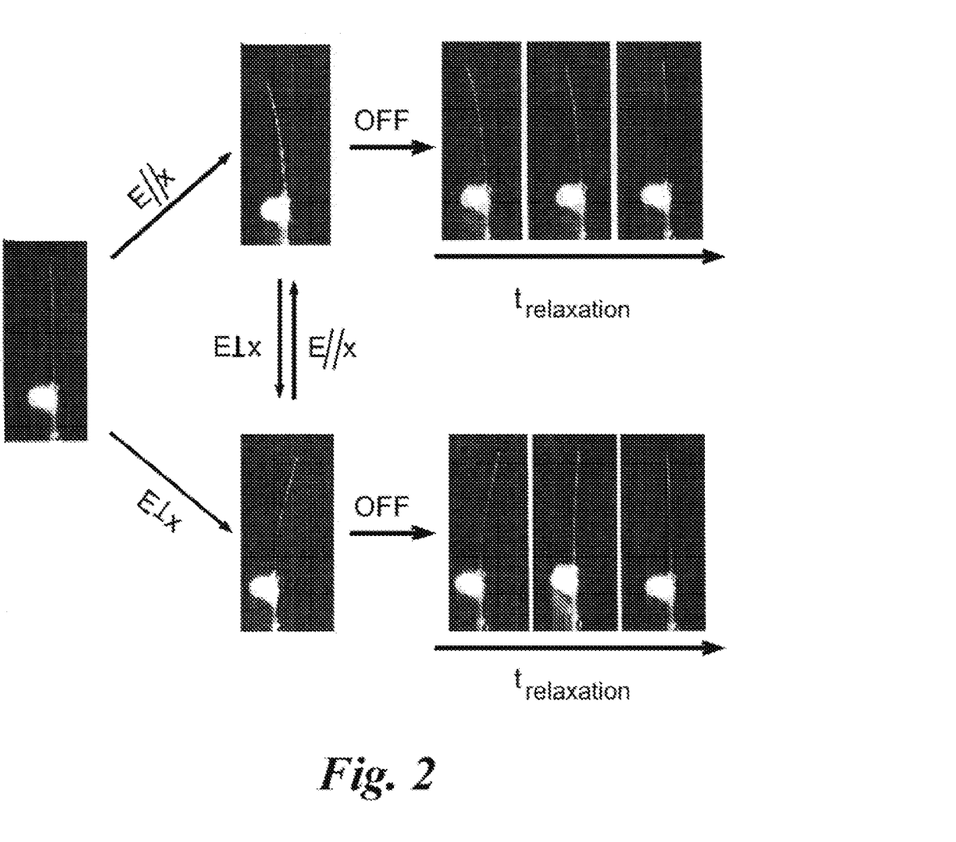
FIG. 2 illustrates the shape-relaxing (photoelastic) of cantilevers comprising azo-CP2-20 following removal of the 442 nm light source at irradiance of 120 $mW/cm^2$.

The photoresponse of glassy poly-domain azobenzene liquid-crystalline network (azo-LCN), when exposed to 442 nm laser, exhibits slight larger magnitude bending, identical polarization dependence, and retains the bent shape for an extended (months) period of time (known as photo-fixing effect). As shown in FIG. 2, the response of azo-CP2-20 after removal of the incident light source is evidently different. The cantilever can be reversibly and repeatedly bent forward and backward and remains bent to continuing exposure. However, after removal of the 442 nm light (of any polarization direction), the cantilever rapidly (about 10 min) restores to the original vertical position, as depicted in FIG. 1A, indicating that there is practically no photo-fixing behavior in these azo-CP2-XX polymers.

Figure 3:
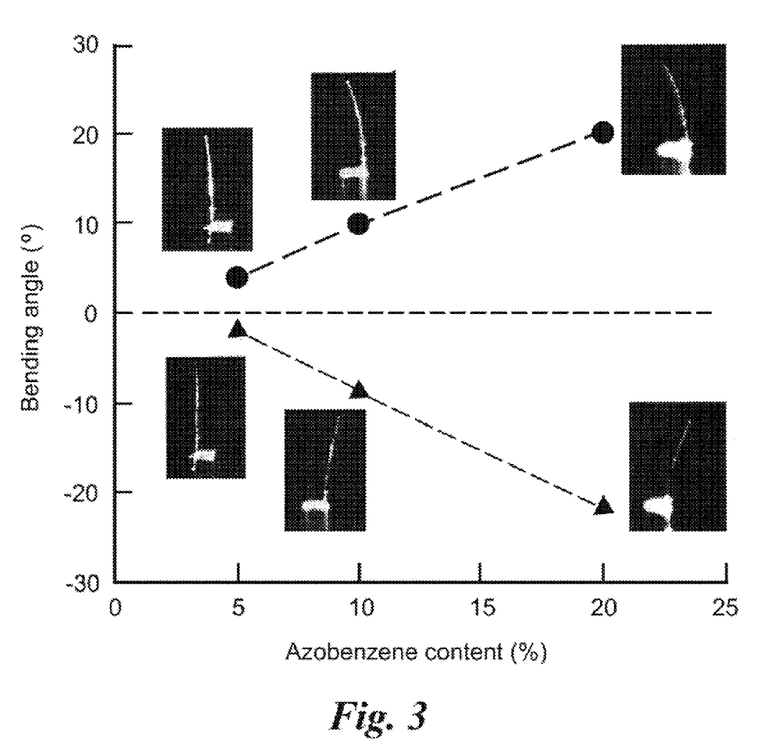
FIG. 3 illustrates the photodirected bending of cantilevers comprising azobenzene-containing polyimide with increasing concentrations of azobenzene (5-20 mol %) in response to the exposure to E//x (●) and E⊥x (▲) of a 442 nm light source at 120 $mW/cm^2$.

To further understand the relationship between azobenzene/crosslinker concentration and the resulting photoresponse of the azo-CP2 materials, FIG. 3 plots the maximum bending angle as a function of azobenzene concentration for exposure of cantilevers to a 120 mW/cm², 442 nm laser that is polarized parallel to (E//x) or orthogonal (E⊥x) to the long axis of the cantilever. Reversible bidirectional bending is observed for all three samples with the magnitude of bending angle increasing with increasing azobenzene concentration. As evident from Table 1, the increase in azobenzene concentration not only influences the optical properties of the films (i.e. an increase in absorption coefficient), but also increases the crosslink density (as indicated by the decrease in the average molecular weight of linear segment or $M_c$) and the $T_g$ of azo-CP2 networks. Both of these factors are known to strongly influence the resulting photomechanical outcome in analogous glassy azo-LCN.

Although specific embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:

1. A cross-linked polyimide having three branches and the following general structure:

wherein n, m, and l are degrees of polymerization of each of the three branches of the cross-linked polyimide; and wherein R' is selected from the group consisting of —C(CF$_3$)$_2$—, —O—, —SO$_2$—, >C(=O), —OPh-C(CH$_3$)$_2$-PhO-, -(Ph)C(CF$_3$)—, a direct bond (—), and mixtures thereof.

2. The cross-linked polyimide of claim 1 wherein n, m, and l are equal.

3. The cross-linked polyimide of claim 1 wherein at least one of n, m, and l are not equal.

4. The cross-linked polyimide of claim 1 wherein n, m, and l are from about 2 to about 20.

5. The cross-linked polyimide of claim 2 wherein n, m, and l are from about 3 to about 15.

6. A method for making the crosslinked polyimide of claim 1 comprising the following steps:

dissolving a bis(phthalic anhydride) compound having a general structure:

and 1,3-bis(3-aminophenoxy)benzene in N,N-dimethylacetamide to form a solution;

stirring the solution under a nitrogen atmosphere at room temperature to form a poly(amic acid) oligomer solution comprising poly(amic acid) oligomers, the poly(amic acid) oligomers further comprising terminal anhydride groups;

adding a tris(azobenzene-amine) cross-linker to the poly(amic acid) oligomer solution, wherein the tris(azobenzene-amine) cross-linker has a general structure:

wherein for meta-azo substitution, R is equal to H, and for para-azo substitution, R is selected from the group consisting of H, F, Cl, CF$_3$, and CH$_3$;

allowing the tris(azobenzene-amine) cross-linker to dissolve in the poly(amic acid) oligomer solution to form a poly(amic acid) sol-gel precursor; and curing the poly(amic acid) sol-gel precursor to crosslink and imidize the poly(amic acid) sol-gel precursor to form the crosslinked polyimide.

7. The method of claim 6 wherein a molar ratio of the bis(phthalic anhydride) compound to the 1,3-bis(3-aminophenoxy)benzene is from about 1.00:0.92 to about 1.00:0.55.

8. The method of claim 6 wherein the bis(phthalic anhydride) compound is 2,2-bis(phthalic anhydride)-1,1,1,3,3,3-hexafluoroisopropane.

9. The method of claim 6 wherein the bis(phthalic anhydride) compound is 4,4'-oxydiphthalic anhydride.

10. The method of claim 6 wherein the bis(phthalic anhydride) compound is 3,3',4,4'-benzophenonetetracarboxylic dianhydride.

11. The method of claim 6 wherein the bis(phthalic anhydride) compound is 3,3',4,4'-diphenylsulfone tetracarboxylic dianhydride.

12. The method of claim 6 wherein the bis(phthalic anhydride) compound is 2,2-bis[4-(3,4-dicarboxyphenoxy)phenyl]propane dianhydride.

13. The method of claim 6 wherein the bis(phthalic anhydride) compound is 4,4'-(2,2,2-trifluoro-1-phenylethylidene) diphthalic anhydride.

14. The method of claim 6 wherein the bis(phthalic anhydride) compound is 3,3',4,4'-biphenyl-tetracarboxylic dianhydride.

* * * * *